United States Patent
Chambers et al.

(10) Patent No.: US 6,302,919 B1
(45) Date of Patent: Oct. 16, 2001

(54) REVERSE-FLOW CENTRIFUGAL FILTRATION METHOD

(76) Inventors: Brian Chambers, 4778 Cass St. Apt. #B, San Diego, CA (US) 92109; Adam Sampson, 9540 Towne Center Dr., San Diego, CA (US) 92121; Matt McDermott, 9971 Scripps Westview Way, #13, San Diego, CA (US) 92131; Byron Knight, P.O. Box 7396, San Diego, CA (US) 92167; Gunars E. Valkirs, 2893 Paseo Del Sol, Escondido, CA (US) 92025; Howard J. Kirchick, 5449 Panoramic La., San Diego, CA (US) 92121

( * ) Notice: Subject to any disclaimer, the term of this patent is extended or adjusted under 35 U.S.C. 154(b) by 0 days.

(21) Appl. No.: 09/358,130

(22) Filed: Jul. 20, 1999

(51) Int. Cl.[7] .................................................. B01D 21/26
(52) U.S. Cl. .................... 2190/781; 210/782; 210/360.1; 210/518
(58) Field of Search ..................................... 210/780, 781, 210/782, 117, 324, 359, 360.1, 515, 516, 518

(56) References Cited

U.S. PATENT DOCUMENTS

| | | |
|---|---|---|
| 3,488,768 | 1/1970 | Rigopulos . |
| 3,799,342 * | 3/1974 | Greenspan ........................... 210/780 |
| 3,960,727 | 6/1976 | Hochstrasser . |
| 4,522,713 | 6/1985 | Nussbaumer et al. . |
| 4,600,507 | 7/1986 | Shimizu et al. . |
| 4,602,995 | 7/1986 | Cassaday et al. . |
| 4,832,851 | 5/1989 | Bowers et al. . |
| 5,786,228 | 7/1998 | Charlton et al. . |

* cited by examiner

Primary Examiner—David A. Reifsnyder
(74) Attorney, Agent, or Firm—Foley & Lardner

(57) ABSTRACT

A filtration device, apparatus, and method of filtration useful for filtering liquid samples are disclosed wherein filtration occurs opposite the direction of centrifugal force. The filtration device is placed within a container that contains the liquid sample to be filtered. Together, the filtration device and the container comprise the filtration apparatus. Centrifugation forces the liquid sample present in the container to enter the filtration device, thereby effecting filtration. The vertical position of the filtration device is fixed within this container during filtration.

9 Claims, 3 Drawing Sheets

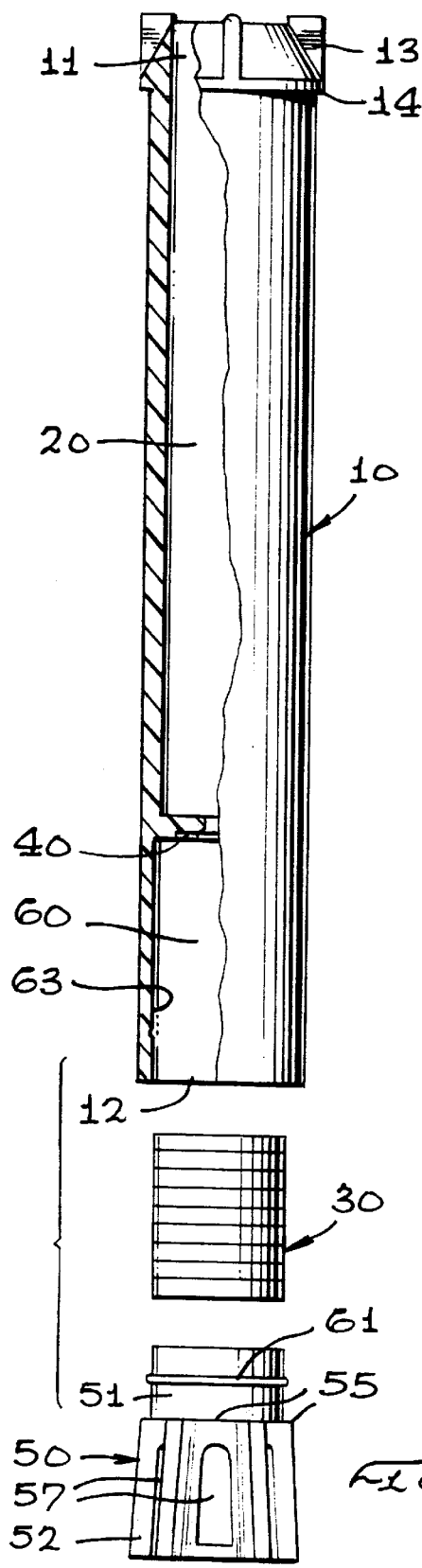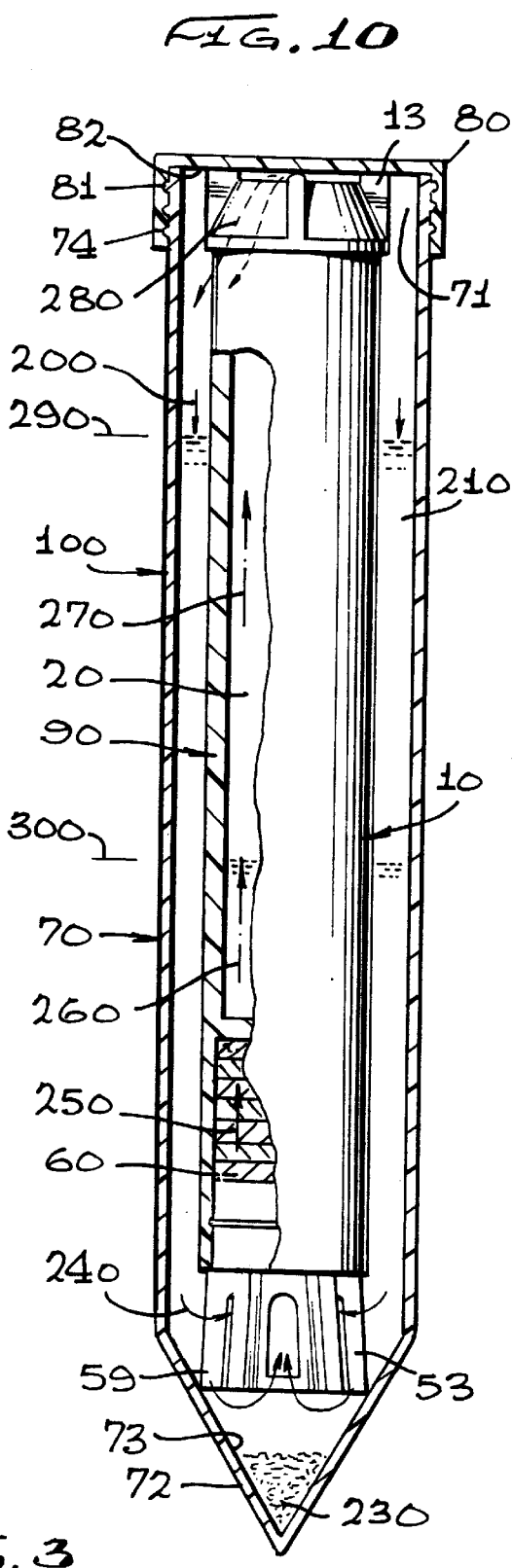

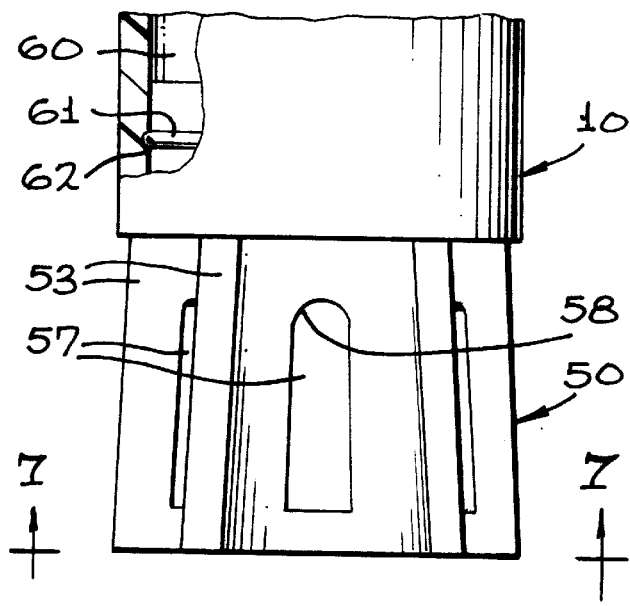
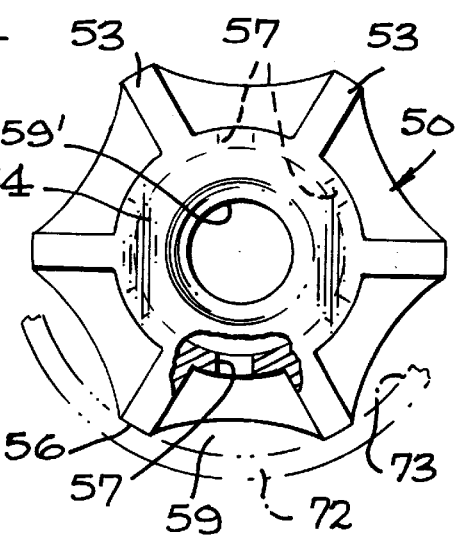
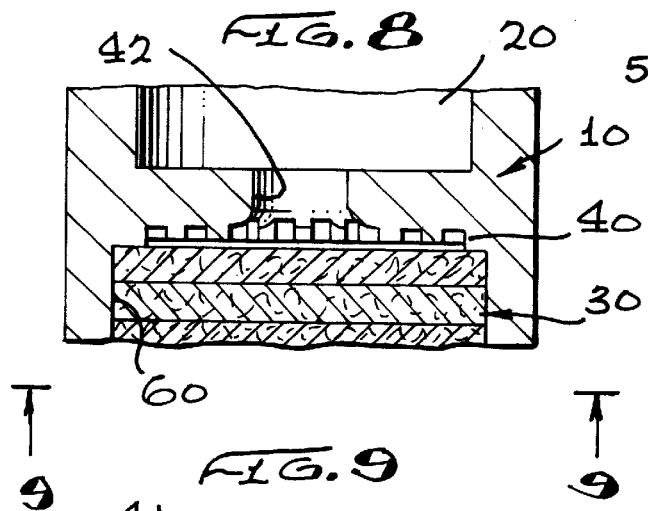
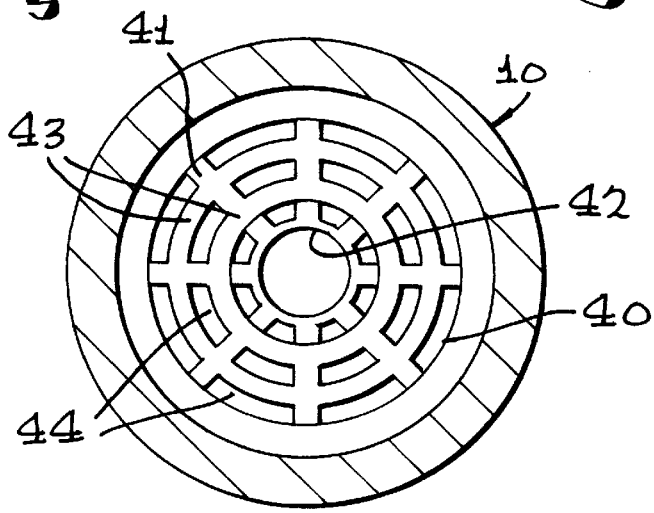
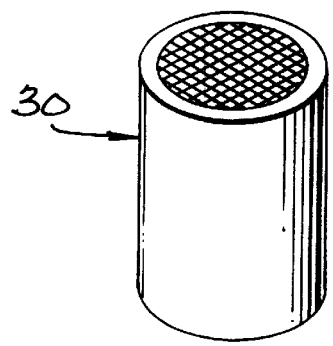

REVERSE-FLOW CENTRIFUGAL FILTRATION METHOD

The present invention relates to a filtration method, apparatus, and device for filtering liquids wherein filtration occurs opposite the direction of centrifugal or gravitational force.

BACKGROUND

The following information is offered solely to assist the understanding of the reader, and none of the information is admitted to describe or constitute prior art to the claims of the present invention.

The process of filtration is necessary to remove undesirable substances from liquids. Such substances can exist in a variety of forms, ranging from large, insoluble material to small, soluble organic or inorganic molecules. Accordingly, each form presents a different challenge to the task of filtration. Complexities arise when several forms of unwanted substances are present in the same liquid solution, i.e. both large and small, soluble and insoluble, particulate and non-particulate, organic and inorganic, etc. Liquids that are uniform in composition are therefore easier to filter, while those with more complex constructions can be more difficult.

This problem becomes particularly evident when a liquid containing insoluble material is filtered, as such material can clog the filtering area. As a result, numerous techniques have been devised to aid in improving the filtration of liquids containing insoluble material. For example, one technique involves dispersing the insoluble material throughout the liquid prior to filtration in order to avoid clogging the filter area. While this approach may initially deter the insoluble material from collecting in the filter area, the material remains present in the liquid and eventually does settle into and clog the filter. Alternatively the insoluble material can actually be removed from the liquid before the filtration process begins. Usually this is achieved with a screen or other straining device, in essence, putting the liquid through an initial filtration. Another method subjects the liquid sample to centrifugation prior to filtration in order to remove the insoluble material. Here, the insoluble material is discarded and the fluid supernatant is filtered. Although techniques that involve the removal of the insoluble material prior to filtration are generally more effective, they do require additional manipulation of the liquid sample, increasing the amount of time spent on the procedure and raising the likelihood of error.

Insoluble materials are often not the sole barriers to successful, efficient filtration The above-described methods often fail to remove large particulate material from liquid samples, as well. Typical approaches for removing these large particulate materials often require sequential filtration processes. Generally, the insoluble or large particulate material is first precipitated via centrifugation. The remaining large unprecipitated particulate material is then removed with an initial filtration step involving a very coarse or porous filtering material. The filtered liquid is then subjected to further filtration as necessary. Again, this lengthens the duration of sample handling, and increases the possibility of error.

Often a liquid sample contains undesirable non-particulate material and several techniques have been devised to neutralize and remove these substances from the liquid sample either prior to or during filtration. While it is sometimes possible to neutralize undesirable non-particulate material by exposing the sample to ultraviolet light, heat, chemical substances, etc., this exposure may also neutralize substances in the sample that are desirable. As with the above-mentioned filtration methods, these techniques increase the number of manipulations necessary to filter the liquid and therefore make them more difficult and costly to perform. Special filtering material may be used as an alternative to the above-mentioned technique for removing undesirable non-particulate material from liquid samples, however, this filtering material often exhibits a limited capacity to remove, absorb and/or neutralize the undesirable non-particulate material. Additionally, this specialized filtering material is often not particularly suited for use in filtering liquids that contain more than one type of undesirable component.

While it is true that the majority of filtration techniques and devices are designed with the filtration of the entire volume of the liquid sample in mind, it is sometimes preferable to filter only a small portion of the total sample. Of those techniques that allow only a small portion of the liquid sample to be filtered, the volume of the resulting filtrate is often not related to the initial volume of the liquid. This may prove unsatisfactory when it is important that the filtrate volume relate directly to the initial volume of the liquid sample prior to being filtered.

For the foregoing reasons, it is clear that there exists a need for a filtration method, apparatus, and device that simply, accurately, effectively, and efficiently remove a wide variety of undesirable substances from a liquid sample in a manner that prevents the filtering area from becoming clogged with the precipitated insoluble and particulate material, without exceeding the filtering capacity of any of the filtering materials, to produce a volume of filtrate that is proportional to the initial volume of the liquid sample.

SUMMARY

The present invention is directed to a filtration method, apparatus, and device that simply, accurately, effectively, and efficiently remove a wide variety of undesirable substances from a liquid sample in a manner that prevents the filtering area from becoming clogged with the precipitated insoluble and particulate material, without exceeding the filtering capacity of any of the filtering materials, to produce a volume of filtrate that is proportional to the initial volume of the liquid sample.

A method of filtering a liquid sample having features of the present invention comprises the steps of placing a liquid sample into a container, inserting a filtration device into the container such that the lower portion of the filtration device is submerged in the liquid sample, and effectuating filtration by subjecting the liquid sample, the container, and the filtration device to centrifugation. A method of filtering a liquid sample in a container having features of the present invention comprises the steps of placing a filtration device in the liquid sample of the container and then subjecting the liquid sample, the container, and the filtration device to centrifugation, where the vertical position of the filtration device relative to the container is fixed by contact between the container and the filtration device. Another method of filtering a liquid sample in a container having features of the present invention comprises the steps of placing a filtration device in the liquid sample, sealing the container, and then subjecting the sealed container containing the liquid sample and the filtration device to centrifugation, where the vertical position of the filtration device relative to the container is fixed by contact between the container and the filtration device.

An apparatus having features of the present invention comprises a container and a filtration device that are related to one another in design so as to provide the benefits of the present invention. A filtration device having features of the present invention is designed to fit within the container such that the vertical position of the filtration device is fixed within the container during filtration. It comprises a filtration housing having a top end and a bottom end, both of which are open, a collection chamber that is located within the filtration housing as an open area, a filter member located beneath the collection chamber facing downward, and a spacer element located beneath the filter member with one or more openings sufficient to render the filter member accessible to the sample.

A filtration device for filtering a liquid sample in a container having features of the present invention comprises a filtration housing having an open top end and an open bottom end, a collection chamber located within the filtration housing, a filter member located beneath the collection chamber, and one or more spacer elements associated with the filtration housing that engage the container and keep the filter member accessible to the liquid sample during filtration, where the filtration device is designed to fit within the container such that the vertical position of the filtration device relative to the container is fixed by contact between the container and the filtration device. Another filtration device for filtering a liquid sample in a container having features of the present invention comprises a filtration housing having an open top end and an open bottom end, a liquid permeable diaphragm located within the filtration housing, a collection chamber located within the filtration housing above the liquid permeable diaphragm, a filtration chamber located within the filtration housing below the liquid permeable diaphragm, a filter member located within the filtration chamber, and a spacer element associated with the filtration housing that engages the container and keeps the filter member accessible to the liquid sample during filtration, where the filtration device is designed to fit within the container such that the vertical position of the filtration device relative to the container is fixed by contact between the container and the filtration device. In this aspect, the spacer element comprises a hollow neck that engages the inner surface of the filtration housing in the filtration chamber beneath the filter member and a hollow body that protrudes from the open bottom end of the filtration housing to engage the inner surface of the container, the body having one or more openings sufficient to render the filter member accessible to the liquid sample.

The present invention is able to remove a wide variety of undesirable substances from a liquid sample simply, accurately, effectively, and efficiently by precipitating insoluble and particulate material from the sample via centrifugation, while filtering the liquid sample in a manner that prevents the filtering area from becoming clogged with the precipitated insoluble and particulate material. Centrifugation forces the liquid sample, as well as any insoluble or particulate matter in the liquid sample, downward. This insoluble or particulate matter collects at the bottom of the container. Because the filtering area of the filtration device is maintained in a position above where the particulate matter collects, this material does not impede the flow of liquid from the exterior of the filtration device into the lower chamber of the filtration device and upward through the filtering area. Moreover, the filter member is kept clear of debris by centrifugal force during filtration. This same force creates pressure on the liquid sample and attempts to equalize liquid levels inside and outside the filtration device. This directs the liquid upward through the filter member into the collection chamber. This "reverse flow", upward and away from the precipitated material at the bottom of the container and against the direction of centrifugal force, coupled with the location of the filter member above the precipitated material, permits the filtration of liquids containing insoluble and particulate matter. Because the movement of this device within the container is prevented, the filter member does not contact the precipitated material.

Additionally, the vertical movement of this device is fixed within the container at a particular position. This permits the user of this apparatus to filter only a portion or subset of the initial sample volume. This can prevent "over-filtration", whereby the effective filtering capacity of a filter material is exhausted by excessive liquid movement through the filter. Filtering only a portion or subset of the initial sample volume also permits more definitive comparisons between and among samples that are filtered. When the resulting volume of the filtered liquid is directly related and/or proportional to the initial volume of the liquid sample prior to being filtered, the relative concentrations of materials present in different liquid samples run at different times can be determined by assaying the relative concentration of these materials in the filtered liquid.

All of the above benefits are provided by the method, apparatus, and device of the present invention when the vertical position of the filtration device is fixed within the container during filtration. Although a wide variety of containers may be used, in each embodiment the filtration device is designed to fit within the container such that the vertical position of the filtration device relative to the container is fixed by contact between the container and the filtration device. In preferred embodiments this contact is between one or more spacer elements and/or one or more contact elements of the device and the container.

In one embodiment, the vertical position of the filtration device is fixed within the container by one or more spacer elements associated with the filtration housing that engage the container. This engagement keeps the filter member accessible to the liquid sample during filtration. In another embodiment, the vertical position of the filtration device is fixed by a spacer element associated with the filtration housing that engages the container and keeps the filter member accessible to the liquid sample during filtration. In this aspect, the spacer element comprises a hollow neck and a hollow body. The neck engages the inner surface of the filtration housing in the filtration chamber beneath the filter member. The body protrudes from the open bottom end of the filtration housing to engage the inner surface of the container. The body has one or more openings sufficient to render the filter member accessible to the liquid sample.

In a preferred embodiment of the invention, the vertical position of the filtration device is fixed within the container because the vertical movement of the filtration device is prevented by contact between the contact elements of the filtration housing, the spacer element, and the container. In a further preferred embodiment, the container used with this filtration device comprises a standard 15 ml conical test tube and a cap that can seal this test tube. In this preferred embodiment, the filtration device is fixed within the test tube by contact between the filtration housing and the cap of the test tube and by contact between the spacer element and the portion of the test tube where it narrows sufficiently to contact the spacer element. In another aspect of this preferred embodiment, where the spacer element is an extension of the filtration housing, the filtration device is fixed by contact as above, except it is an extension of the filtration housing that functions as the spacer element.

Generally, the filter member can comprise many different types of filtering materials, filters, and supports, and be present in many different forms. As used herein, the terms "filter", "filter material" and "filtering material", as well as the plural forms of these terms, are used interchangeably. They refer generally to material acting as a filter, as that term is commonly used, and as that term is used by those of skill in the art. Without intending to limit the meaning of these terms, they can be understood to include material capable of removing, adsorbing, separating, and/or neutralizing one or more substances.

In one embodiment of the invention, the filter member is in the form of a liquid permeable cartridge that encloses one or more filters. In another embodiment of the invention, the filter member comprises a plurality of filters. In a preferred embodiment, the filter member comprises one or more filters that are supported on the top by a liquid permeable diaphragm that defines the bottom of the collection chamber, and are supported on the bottom by the top of the spacer element. This collection of stacked filters and/or filtering material is also referred to as a filter stack. In this embodiment of the invention, the filters and/or filtering materials may also be self-supporting.

Generally, if more than one filter or filtering material is used, the filters or filtering materials will be arranged to provide the most effective filtration possible. In one embodiment of the invention, the filters and/or filtering materials are arranged to filter successively smaller particulate materials. In this manner, more coarse or porous filters and/or filtering materials are generally located upstream from more fine, restrictive filters and/or filtering materials. However, the arrangement may vary such that the order of the filters and/or filtering materials meets other filtration needs, including support and spacing requirements.

Generally, the filter, filters, and/or filtering materials will be chosen to remove whatever undesirable substances are likely to be present in the liquid to be filtered. Typically more porous filters will be chosen to filter larger material and less porous filters will be chosen to filter smaller material. In one embodiment of the invention, one or more filters and/or filtering materials removes insoluble material that was not successfully precipitated. In another embodiment of the invention, one or more filters and/or filtering materials remove particulate material. In still another embodiment of the invention, one or more filters and/or filtering materials removes non-particulate material. In still other embodiments of the invention, one or more filters and/or filtering materials removes organic substances or inorganic substances. In further embodiments, one or more filters and/or filtering materials removes combinations of the above. In one preferred embodiment of the invention, one or more of the filters removes, absorbs, or neutralizes one or more non-particulate materials. In a further preferred embodiment the substance that is removed, absorbed or neutralized is alkaline phosphatase.

In another aspect of the present invention, the filtering capacity of the filtration device can be utilized to isolate, separate, concentrate, or otherwise purify one or more desirable substances from the liquid sample. Following filtration, these substances may be collected, isolated or otherwise generally reconstituted from the filter material. In a preferred aspect, the desired materials are present in a discrete portion of the filter member so they can be separated from the filtration device more easily. In a further preferred aspect, the filter member is in the form of a cartridge easily removed from the device.

Generally, there are several advantages associated with fixing the vertical position of the filtration device relative to the container. In particular, when such an apparatus is used, it is possible to prevent the filter member from contacting precipitated insoluble material that might collect at the bottom of the apparatus, which can occur when a liquid sample that contains insoluble material is subjected to centrifugation. This advantage is realized in one embodiment of the invention, where the vertical position of the filtration device of the apparatus remains fixed during filtration relative to the container of the apparatus, in order to prevent the filter member from contacting precipitated material.

But other advantages flow from maintaining the vertical position of the filtration device relative to the container. For example, in another embodiment, fixing the vertical position limits the volume of the liquid filtered. This may prevent the limited filtering capacity of one or more of the filters and/or filtering materials from being exceeded by one or more substances in the sample that are to be filtered. Likewise, in other preferred embodiments the volume of the filtrate is relatively constant with respect to the volume of the liquid sample. In still further preferred embodiments, the above embodiments are present in combination.

The method, apparatus, and device of the present invention can have many applications. They can be used to remove a wide variety of undesirable substances from a liquid sample. While not intending to present an exhaustive list, these substances, also referred to as "impurities," can include material such as whole cells, cell fragments, large proteins, peptides, amino acids, antibodies, carbohydrates, sugars, steroids, fatty acids, and lipids; nucleic acids like DNA, RNA, cDNA (complementary DNA), tRNA, etc., oligonucleotides, and nucleotides; chemical or enzymatic substances like salts, sodium chloride, arsenic, benzene, bile, alkaline phosphatase, protein kinases, etc.; metal ions like iron, lead, copper and their salts; and, dissolved gases like chlorine, nitrogen, carbon dioxide, and oxygen. Organisms such as bacteria, yeast, fungi, viruses, intestinal parasites, water-born parasites, and the like are also considered impurities.

Whereas the removal of "impurities" may be desired in some applications, their presence in the filtrate may be desired in other applications, such as when their presence is determinative of a characteristic or quality of the liquid sample, and this characteristic or quality is being qualified or quantified. So in certain applications, filter material may be selected to permit the passage through the filter of substances such as those listed above as "impurities". In other applications, the "impurities" are removed by filtration so they may be collected. In still other applications, the presence of these substances in the filtrate is not desired. In any case, selecting filters appropriate for each application is with the skill of those in the art.

To assist the understanding of the reader, the following categories have been established to describe, but not enumerate or otherwise limit, the various types of undesirable substances that may be present in a liquid sample.

In general these impurities may be classified either as soluble or insoluble material. For the purpose of clarification, the term insoluble is given its ordinary meaning but is also used here in a more specific sense to connote a property of a substance that permits it to be precipitated by centrifugation. In contrast, soluble materials are substances that are not effectively precipitated via centrifugation.

In general, impurities may also be classified as particulate or non-particulate material. Particulate material my either be soluble or insoluble, with the term insoluble referring to those particulate materials that are precipitated during centrifugation and the term soluble referring to those particulate materials that are not precipitated by centrifugation. What is meant by non-particulate material is a substance that is generally soluble.

The term "centrifugation" is well known in the art and refers to the application of centrifugal force. What is meant by "standard 15 ml conical tube" is a type of test tube that is typically used by those in the sciences. Representative examples of standard 15 ml test tubes include those available from Fisher Scientific: Fisherbrand (Cat. No.: 05-527-45); Corning (Cat. No.: 430055; or Falcon (Cat. No.: 352095), or similar tubes of comparable size and shape. Clearly, however, containers of other sizes and shapes could also be used with the present invention. One particular container readily suited for use with the present invention is the standard 50 ml conical test tube such as those available from Fisher Scientific: Fisherbrand (Cat. No.: 14-375-150); Corning (Cat. No.: 430828); or Falcon (Cat. No.: 352070), or similar tubes of comparable size and shape. Irrespective of the size, shape, and type of container employed for use with the device of the present invention, it is understood that the device, when used with a particular container, would be designed for use with that particular container such that, together, they would provide all of the benefits realized (explicitly and/or inherently) by the present invention.

In various aspects of the invention, one or more spacer elements are associated with the filtration housing. The term "associated with" is used here to describe the relationship between these elements. It is intended to convey, collectively, one or more spacer elements that is/are separate from but functionally connected to the filtration housing, and one or more spacer elements that is/are contiguous with or a part of the filtration housing itself, or an element associated with the filtration housing. The spacer element(s) engage the container and keep the filter member accessible to the liquid sample during filtration.

Other aspects of the invention that are not pictured here comprise a plurality of spacer elements. These spacer elements are associated with the filtration housing and engage the container. In doing so, they keep the filter member accessible to the liquid sample during filtration.

The phrase "filter member" is used to describe one or more filters or filter materials and related supports, if necessary. A filter member may be a single filter or filter material. Alternatively a filter member may be made up of numerous filters or filtering material and these may be all of the same type or may be of different types.

The term "kit" refers to a collection of material sold together. These materials are normally related with respect to their use in a particular application. One application, for example, is the detection of enteric pathogens. So a kit directed to detecting enteric pathogens would comprise material related to this detection. The term "assay" when used in the context of describing a kit is used to denote a particular application.

Despite the specific examples provided above, the elements of the filtration device, filtration apparatus, container and cap may take many forms, may be arranged in many ways, and be comprised of many different substances and/or materials. One of skill in the art would know how to select the appropriate substances and/or materials specific for each intended use.

BRIEF DESCRIPTION OF THE DRAWINGS

These and other features, aspects, and advantages of the present invention will become better understood with regard to the following description, appended claims, and accompanying drawings where:

FIG. 3 shows an exploded elevation of one embodiment of the filtration device.

FIG. 4 shows a top perspective of an alternative embodiment of the present invention referred to as a cartridge-type filter member.

FIG. 6 shows an enlarged fragmentary side elevated view of the lower portion of one embodiment of the filtration device.

FIG. 7 shows a view taken on line 7—7 of FIG. 6, partially broken away.

FIG. 8 shows a partial cross-sectional view taken at arrow 8 of FIG. 2.

FIG. 9 shows a sectional view on line 9—9 of FIG. 8.

FIG. 10 shows an assembled view of the complete, sealed apparatus of one preferred embodiment.

Note that the drawings are not necessarily to scale and that certain features of the invention may be exaggerated in scale and shown in schematic form in the interest of clarity and conciseness.

DETAILED DESCRIPTION OF THE PREFERRED EMBODIMENTS

Figure 1:
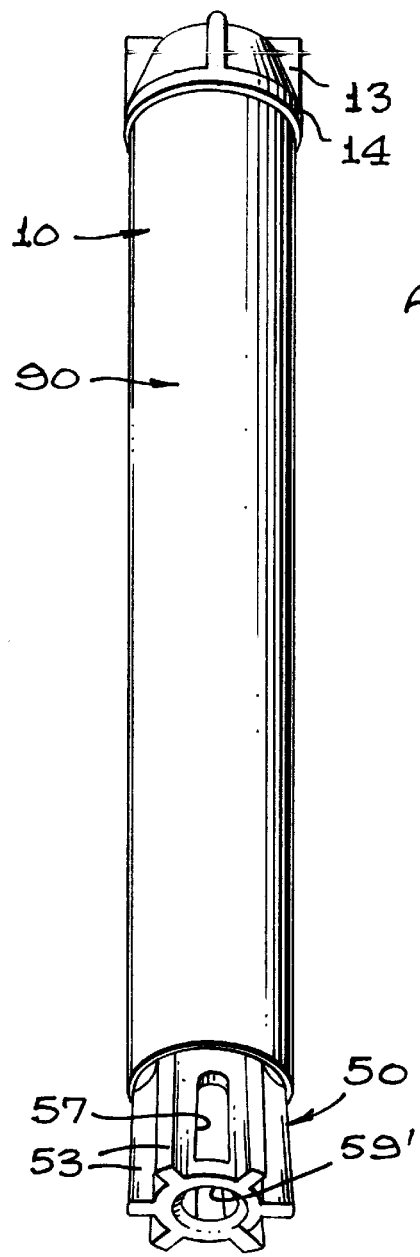
FIG. 1 shows a bottom perspective of one embodiment of the filtration device.
Figure 5:
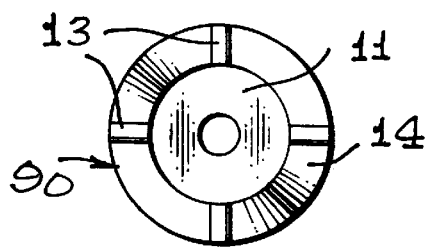
FIG. 5 shows a plan view taken on line 5—5 of FIG. 2.
Figure 2:
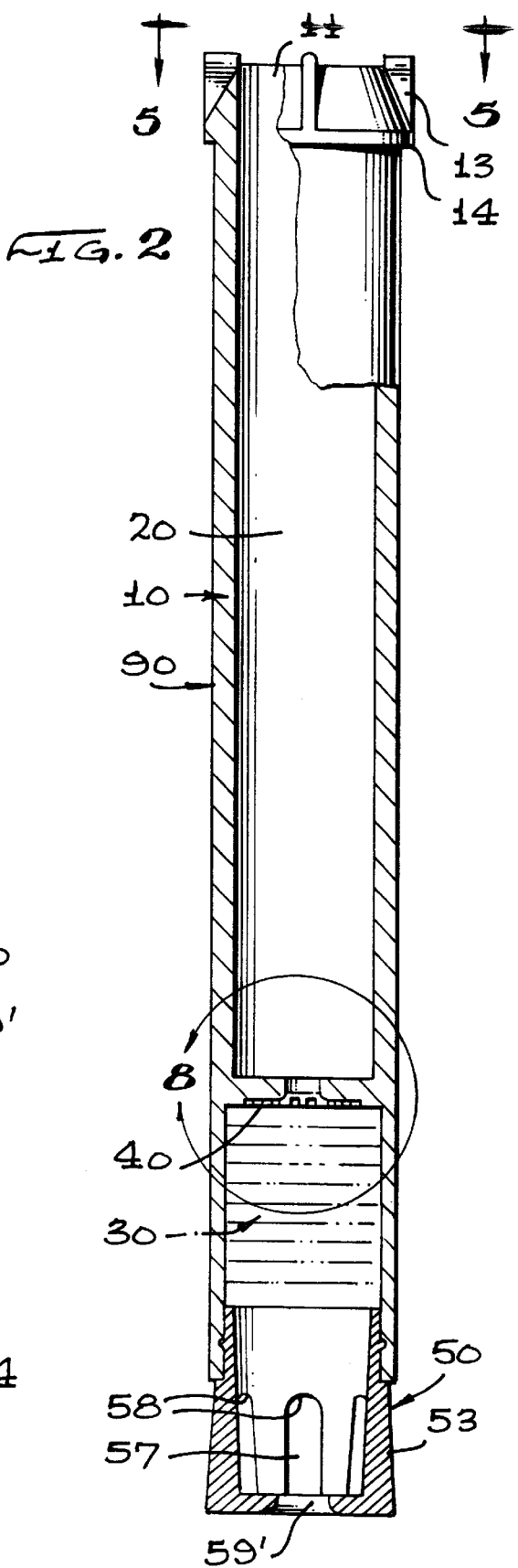
FIG. 2 shows a side elevation, partially broken away, of one embodiment of the filtration device.

One preferred embodiment of the filtration device of the present invention is illustrated in FIGS. 1–3, and 5–10, with an alternative aspect of the filter member illustrated in FIG. 4. As shown in these figures, the filtration device of this preferred embodiment comprises a filtration housing 10 enclosing a collection chamber 20 located above a filter member 30. This filter member 30 is separated from the collection chamber 20 by a liquid permeable diaphragm 40. A spacer element 50 is located beneath the filtration housing 10, extending outward. The outer diameter of the spacer element 50 is slightly smaller than the inner diameter of the filtration housing 10 providing for a snug fit.

In the aspect of the preferred embodiment illustrated in FIGS. 1–3 and 5–10, the filter member 30 comprises a collection of filters or filtering materials. In this aspect, support for the filters are provided by the filters themselves, by the liquid permeable diaphragm 40, and by the spacer element 50. The top portion of the filtration housing 10 is shaped to provide firm contact with the interior of the related container.

More specifically, in this preferred embodiment of the present invention, the filtration housing 10 is an elongate hollow cylinder with an open top end 11 and an open bottom end 12. Four contacting or contact elements 13 protrude from a contact ring 14 located at the open top end of the filtration housing 11. The collection chamber 20 is defined at its bottom end by a liquid permeable diaphragm 40 that separates the filtration housing 10 into an upper collection chamber 20, and a lower chamber 60 defined at its upper end by the liquid permeable diaphragm 40 and at its bottom end by the open bottom end of the filtration housing 12. This lower chamber 60 will be referred to as the filtering chamber and as the filtration chamber. These two terms are used interchangeably. The liquid permeable diaphragm 40 that separates the collection chamber 20 from the filtering chamber 60 contains support ribs 41 radiating from a central spoke 42. One or more concentric support rings 43 surround the central spoke 42 and, together, the central spoke 42, support rings 43, and support ribs 41, define open spaces 44 that permit the passage of fluid. Beneath the liquid permeable diaphragm 40 and located within the filtering chamber 60 is the filter member 30.

In its most preferred embodiment, the filter member 30 comprises five filters, all of a diameter that affords a snug fit against the wall of the filter chamber. The first filter (in the direction of sample filtration) is a cellulose filter with a pore size of approximately 8–10 $\mu$m and a thickness of about 4 mm. The second and third filters are identical and are cellulose filters with diatomaceous earth that have the same dimensions as the cellulose filter and a pore size of about 4–6 $\mu$m. The fourth filter is from Porex Technologies, the material is UHMW P.E., IRM-0269, the pore size is about 10 $\mu$m and the thickness is approximately the same as the first three filters. The final filter is Whatman GF/F filter paper that has a pore size of about 0.7 $\mu$m and a thickness of about 0.4 mm. The cellulose and diatomaceous earth filters serve as course filters that remove gross particulates and they also adsorb certain organic substances, such as endogenous alkaline phosphatases that may be present in the sample. The Porex filter is a fairly rigid plastic that acts as a support for the diatomaceous earth filters and the GF/F filter. The GF/F filter acts as a finer filter that removes the smaller particulates.

In another preferred embodiment of the present invention the filter member 30 is present in the form of a cartridge as shown in FIG. 4. Here the filter member 30 comprises one or more filtering materials or filters enclosed within a cartridge type support. This cartridge is liquid permeable both on its top and bottom ends thereby allowing liquid to pass through the supporting portions of the cartridge and to enter and pass through the enclosed filters or filtering material. One benefit of the cartridge form of the filter member 30 is that such filter members are readily interchangeable. Multiple cartridge-type filter members 30 having altered filtering characteristics may be selected for use with a single device.

The filter member is designed to fit tightly within the filtration housing 10. This prevents "blow-by", which occurs when liquid sample is able to bypass the filter material of the filter member 30 and enter the collection chamber 20. Blow-by can be prevented by various design features including washers, supports, o-rings, gaskets, and the like. For example, in the preferred aspect of an embodiment of the invention illustrated in FIGS. 1–3 and 5–9, there is a crush ring at the outer diameter of the frit network illustrated in FIG. 9 that acts as a seal between the filter stack 30 and the filtration housing 10, particularly the GF/F filter of the filter stack. Unfortunately, this feature is not illustrated.

The filter member is "facing downward" or "downward facing" in the sense that filtration occurs prior to the liquid entering the collection chamber. If any filter or filtering material, or any arrangement of filters or filtering material, has a specific orientation requirement with respect to the flow of liquid, the orientation will be such that the first surface to be contacted by liquid will be facing outward from the collection chamber towards the bottom of the container.

Beneath the filter member 30 and located partly within the chamber 60 is the spacer element 50. In the preferred embodiment illustrated here, the spacer element 50 comprises a neck 51 and a support base 52, both of which are "hollow" in the sense that they allow the liquid sample in the container to access the filter member 30. In this preferred embodiment, the neck 51 of the spacer element is a hollow cylinder with an outer circumference only slightly less than the inner circumference of the filtration housing 10 that defines the filtering chamber 60, thereby providing a snug fit.

In a further preferred embodiment, the neck 51 and the filtration housing 10 are both tapered so that the outer diameter of the neck 51 is eventually equal to the inner diameter of the filtration housing 10. As the spacer element neck 51 is inserted into the filtering chamber 60, contact is gradually established until the inner diameter of the filtering chamber 60 and the outer diameter of the spacer element neck 51 are the same.

In a further preferred aspect of this embodiment, spacer element neck 51 has one or more crush ribs that help hold the spacer element in the filtration housing. (Not shown). In another further preferred aspect of this embodiment, spacer element neck 51 has one or more snap rings 61 that help hold the spacer element in the filtration housing through contact with one or more corresponding snap ring receivers 62 located on the inner surface of the filtration housing 63 within the filtering chamber 60 (a.k.a. the filtration chamber 60).

The support base 52 of the spacer element 50 comprises several spacer fins 53. These spacer fins 53 radiate from, and are connected to, a central spacer spoke 54. The bottom surface of the central spacer spoke 54 is co-planar and flush with the bottom of the spacer fins 53, providing a flat bottom end. Each of the spacer fins 53 protrude outward, providing a spacer lip 55 that together form a spacer ring 56 of a circumference larger than the inner circumference of the portion of filtration housing 10 that defines the filtering chamber 60. Contact between the spacer ring 55 and the filtration housing 10 limits, determines and supports the insertion of the neck 51 of the spacer element into the filtering chamber 60. An area referred to as the spacer area 57 is created between the spacer fins 53. This spacer area 57 is below, yet in fluid communication with, the filtering chamber 60. Liquid access is permitted via the internal liquid access area 59', which is the area defined by the hollow cylinder of the spacer neck 51. The spacer area 57 communicates with the exterior of the filtration device through several spacer arches 58. Liquid external to the filtration device can pass by and around areas of contact between the device and the container to access the filter member 30 via the external liquid access areas 59, as defined by the container and the spacer fins 53.

A preferred embodiment of the apparatus of the present invention is shown in FIG. 10. Here, a container 70 and a cap 80 are in the form of a standard 15 ml. conical test tube and test tube cap, respectively. The filtration device 90 is designed to fit within the container 70 and remain fixed during filtration. The conical test tube container 70 is an elongate, hollow cylinder open at the top end 71 and closed at a tapered bottom end 72. The inner surface diameter of the bottom end 73 becomes successively smaller until it tapers to a point. The top end 71 is threaded 74 to receive a cap 80. The cap 80 is also threaded 81 to engage the threaded portion 74 of the container.

The filtration apparatus 100 of the preferred embodiment shown here comprises a filtration device 90, a container 70, and a cap 80. Contact is established between the filtration device 90 and both the container 70 and the cap 80. The contact element 13 of the filtration device contacts the inner surface of the cap 82, when the cap threads 81 have fully engaged the container threads 74 so that the container is sealed. The spacer fins 53 of the filtration device contact the inner surface of the bottom end of the container 73.

As shown in FIG. 10, when the apparatus of the present invention is loaded with sample and subjected to centrifugal force 200, the centrifugal force exerts a downward pressure 200 on the liquid sample in the container 210. This force causes the precipitated materials to collect at the bottom of the container 230 while simultaneously creating a force that is exerted on the liquid exterior to the filtration device. In response to this force liquid flows upward 240, opposite the direction of centrifugal force 200, through the filter member 250, and collects in the collection chamber 260. This filtered liquid is known as filtrate 260.

As the liquid sample enters the collection chamber, the level of the height of the column of liquid in the container decreases from its initial height 290 to, ultimately, a final height 300. In one aspect of the preferred embodiment, the final height of the column of liquid in the container 300 is approximately equal to or equals the height of the column of filtrate in the device following filtration. As the volume of filtrate increases, air present in the collection chamber 270 flows out of the collection chamber through gaps between the contacting elements 13. The air 280 replaces the volume of liquid sample lost during filtration as it enters the container.

The function of the filtration housing 10 is to embody the components of the filtration device. The top end 11 is open to allow sample "filtrate" to be withdrawn following filtration. The bottom end 12 is open to allow liquid sample exterior to the filtration device to enter the filtration device and contact the filter member 30. The four contacting elements 13 that protrude from contact ring 14 on the open top end of filtration housing 11 are the elements that make contact with the inner surface of the container's screw cap. These four contacting elements also serve to allow free movement of air 270 displaced by filtrate moving into collection chamber 20 from the area exterior to the device. As the air leaves the collection chamber it replaces the volume of liquid forced from the area exterior to the filtration device.

In this preferred embodiment, the contact elements function to fix the vertical position of the filtration device during filtration. Similarly, the function of the contact ring 14 is to limit, to some extent, the horizontal and vertical position of the filtration device during filtration. The contact ring 14 also serves as a splash guard that helps prevent unfiltered material exterior to the device from splashing, sloshing, or otherwise entering the collection chamber 20 and thus contaminating the filtrate 260.

The function of the collection chamber 20 is to collect filtrate after it has passed through the filter member. The function of the filter member is to remove undesirable substances and/or impurities from the liquid sample prior to its movement into the collection chamber. In the preferred embodiment, the liquid permeable diaphragm 40 acts to separate the collection chamber from the filtration chamber and may also function to support the filter member 30. In one aspect of the invention, the diaphragm also functions to enclose and/or support a filter or filtration material. Together, the support ribs 41, the central spoke 42, and the support rings 43 function to provide a support for the filter member 30 while still allowing open spaces 44 so that liquid may pass through from the filter member into the collection chamber. The function of the spacer element 50 in one aspect of the preferred embodiment is to fix the vertical position of the filtration device within the apparatus during filtration.

In a preferred embodiment, the neck of the spacer element functionally engages the inner portion of the filtering chamber 60, thereby affixing the position of the spacer element relative to the filtration housing. This engagement is enhanced in a further preferred embodiment by the interaction of one or more snap rings 61 with one or more snap ring receivers 62. The lower portion of the spacer element is comprised of a support base 52, which provides the function of fixing the vertical position of the filtration device during filtration. It comprises spacer fins 53 that contact the inner surface of the container, a spacer spoke 54 that functions to stabilize the lower end of the spacer fins and, together, the spacer fins and spacer spokes enclose a spacer area 57 that, by means of spacer arches 58, allows liquid to pass from the exterior of the filtration device to the interior of the filtration device. Together, the spacer lip and spacer ring function to limit the extent by which the neck of the spacer element is inserted into the filtering chamber. The filtering chamber is an open area in fluid communication with the hollow cylinder of the spacer element neck which is itself in fluid communication with the spacer area 57 which, again, is in fluid communication with the exterior of the filtration device. Some or the entire filtering chamber contains a filter member 30. The function of the filter member 30 is to provide a mechanism by which undesirable substances and impurities are removed from the liquid sample.

The function of the container 70 of the apparatus is to enclose the liquid sample and to provide a vessel in which the filtration device can operate.

Both the above device and apparatus can be made from materials well known to those in the art. In the preferred embodiment discussed above, the following materials were used. Generally, the filtration device, container, and cap are made of plastic. Specifically, the main body of the filtration housing in the preferred embodiment disclosed above is made of K-resin. In the same embodiment, the spacer element was made from polypropylene. These materials were chosen because K-resin is more translucent than polypropylene and may be somewhat more durable than the more translucent crystal styrene. Visibility is important so that the markings on a transfer pipette used to remove the filtrate from the collection chamber can be readily distinguished.

Generally, the filters and filtering material used can vary widely, depending on the amount, degree and type of undesirable substances and/or impurities to be removed from the liquid sample. In the preferred embodiment disclosed above, five filters are used, as described previously.

In general terms, the intended use of one preferred aspect of the apparatus is to clarify a set volume of a particulate biological fluid to a predetermined fraction of the starting volume. For any given starting volume, the filtrate volume will be a consistent fraction of the starting volume. Specimen so clarified can then be used for a variety of purposes, including, but not restricted to, medical diagnostic tests.

EXAMPLES

The following example serves to illustrate the method, apparatus, and device of the present invention. This example is in no way intended to limit the scope of the invention.

Example I

Use of the Present Invention for Diagnostic Testing of Enteric pathogens

One intended use of a preferred embodiment is to clarify approximately 0.7 ml of a 5.2 ml suspension of stool diluted approximately 1:10 in a specimen diluent. The clarified specimen can then be used in diagnostic tests for enteric pathogens. In addition to the removal of particulate material, the filters chosen for the preferred embodiment adsorb alkaline phosphatase contained in the stool specimen. The procedure for testing for enteric pathogens using a preferred aspect of the invention, in which the container of the apparatus is a 15 ml conical tube, is as follows:

1. 4.7 ml of specimen diluent is added to the container, here a 15 ml conical tube. Typically, this diluent is a buffered protein solution with detergent. The diluent facilitates solubilization of some substances and also inhibits the nonspecific binding of desirable components to the filtering material.
2. For liquid specimens (watery diarrhea), 0.5 ml of specimen is added to the conical tube containing the diluent. For solid or semi-solid specimens, a scoop is used which measures approximately 0.5 ml of specimen. A scoop of stool is placed into the conical tube containing the sample diluent and the scoop is twirled until the specimen has dislodged from the scoop.
3. The conical tube is capped and mixed by vortexing for about 10 seconds.
4. The cap is removed and discarded.
5. The centrifugal filtration device is placed inside the conical tube and is forcibly submerged. A clean cap is placed on the conical tube.
6. The filtration apparatus, i.e., the conical tube with enclosed centrifugal filtration device, is subjected to centrifugation at 1500×g for 5 minutes which is sufficient to clarify the specimen and for equilibrium to be reached (no net movement of fluid between the inside and outside of the centrifugal filtration device).
7. The apparatus is removed from the centrifuge and the conical tube is uncapped.
8. The filtered specimen (filtrate) is transferred from the collection chamber of the centrifugal filtration device to an assay device, microtiter plate well, or test tube for diagnostic testing.

One skilled in the art would readily appreciate that the present invention is well adapted to carry out the objects and obtain the ends and advantages mentioned, as well as those inherent therein. The methods, substituents, and target materials described herein as presently representative of preferred embodiments are exemplary and are not intended as limitations on the scope of the invention. Changes therein and other uses will occur to those skilled in the art that are encompassed within the spirit of the invention and within the scope of the claims.

It will be readily apparent to one skilled in the art that various substitutions and modifications may be made to the invention disclosed herein without departing from the scope and spirit of the invention. For example, those skilled in the art will readily recognize that the present methods can incorporate a variety of different materials and can be used in a variety of different applications. Thus, such additional embodiments are within the scope of the present invention and the following claims.

The invention illustratively described herein suitably may be practiced in the absence of any element or elements, limitation or limitations, which is not specifically disclosed herein. Thus, for example, in each instance herein any of the terms "comprising", "consisting essentially of" and "consisting of" may be replaced with either of the other two terms. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

Thus, additional embodiments are within the scope of the invention and within the following claims.

What we claim is:

1. A method of filtering a liquid sample in a container comprising the steps of:

placing a filtration device in the liquid sample;

subjecting the liquid sample, the container, and the filtration device to centrifugation;

wherein the vertical position of the filtration device relative to the container is fixed by the contact between the container and the filtration device, the filtration device comprising:

a filtration housing having an open top end and an open bottom end;

a liquid permeable diaphragm located within the filtration housing;

a collection chamber located within the filtration housing above the liquid permeable diaphragm;

a filter member located beneath the collection chamber bellow the liquid permeable diaphragm; and one or more spacer elements associated with the filtration housing that engage the container and keep the filter member accessible to the liquid sample during filtration.

2. The method of claim 1, where the filter member comprises a liquid permeable cartridge that encloses one or more filters.

3. The method of claim 1, where the filter member comprises a plurality of filters.

4. The method of claim 1, where fixing the vertical position of the filtration device within the container prevents the filter member from contacting precipitated insoluble material.

5. The method of claim 1, where fixing the vertical position of the filtration device within the container limits the volume of liquid filtered.

6. A method of filtering a liquid sample in a container comprising the steps of:

placing a filtration device in the liquid sample;

sealing the container;

subjecting the sealed container containing the liquid sample and the filtration device to centrifugation;

wherein the vertical position of the filtration device relative to the container is fixed by contact between the container and the filtration device, the filtration device comprising:

a filtration housing having an open top end and an open bottom end;

a liquid permeable diaphragm located within the filtration housing;

a collection chamber located within the filtration housing above the liquid permeable diaphragm;

a filtration chamber located within the filtration housing below the liquid permeable diaphragm;

a filter member located within the filtration chamber;

a spacer element associated with the filtration housing that engages the container and keeps the filter member accessible to the liquid sample during filtration, the spacer element comprising:
- a hollow neck that engages an inner surface of the filtration housing beneath the filter member;
- a hollow body that protrudes from the open bottom end of the filtration housing to engage an inner surface of the container, and having one or more openings sufficient to render the filter member accessible to the liquid sample.

7. The method of claim 6, where the sealed container comprises a conical tube closed with a cap and where the vertical position of the filtration device is fixed by contact between the top of the filtration device and the cap and the bottom of the filtration device and the conical tube.

8. The method of claim 6, where the filter member comprises a plurality of filters arranged to filter successively smaller particulate materials and where one or more of these filters removes, absorbs, or neutralizes one or more non-particulate materials.

9. The method of claim 6, where fixing the vertical position of the filtration device within the container limits the volume of liquid filtered and prevents the filter member from contacting precipitated insoluble material.

* * * * *